(12) United States Patent
Lang et al.

(10) Patent No.: US 6,499,560 B1
(45) Date of Patent: Dec. 31, 2002

(54) DISPOSABLE STETHOSCOPE DIAPHRAGM AND DISPENSER

(76) Inventors: Heinrich Lang, 43 Winter Wheat Pl., The Woodlands, TX (US) 77381; Izaak A. Ulert, 2929 Post Oak Blvd., Apt. 402, Houston, TX (US) 77056

(*) Notice: Subject to any disclaimer, the term of this patent is extended or adjusted under 35 U.S.C. 154(b) by 0 days.

(21) Appl. No.: 09/590,871

(22) Filed: Jun. 9, 2000

Related U.S. Application Data
(60) Provisional application No. 60/138,765, filed on Jun. 11, 1999.

(51) Int. Cl.[7] .................................................. A61B 7/02
(52) U.S. Cl. ........................ 181/131; 181/137; 221/266
(58) Field of Search .............................. 181/131, 137; 318/67; 221/175, 176, 263, 266

(56) References Cited

U.S. PATENT DOCUMENTS

| 4,461,368 A | * | 7/1984 | Plourde | 181/131 |
| 4,475,619 A | * | 10/1984 | Packard | 181/137 |
| 4,867,268 A | * | 9/1989 | Ulert | 181/131 |
| 6,019,186 A | * | 2/2000 | Zambrano | 181/131 |
| 6,019,187 A | * | 2/2000 | Appavu | 181/131 |

* cited by examiner

*Primary Examiner*—Khanh Dang

(57) ABSTRACT

A disposable diaphragm assembly for use with al types of conventional stethoscopes and a universal retainer ring for retro-fitting conventional stethoscopes to accept the disposable diaphragm assembly. A novel stethoscope for use with the disposable diaphragm assemblies. A stationary dispenser for the disposable diaphragm assemblies from which the assemblies may be loaded onto either retrofitted conventional stethoscopes or the novel stethoscope of this invention without the assembly being contaminated by the hands of medical personnel. Portable and disposable dispensers which also provide for the loading of the disposable diaphragm assembly in a manner which prevents the assembly from becoming contaminated by the hands of medical personnel.

9 Claims, 5 Drawing Sheets

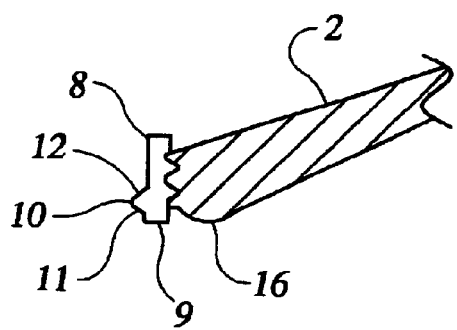
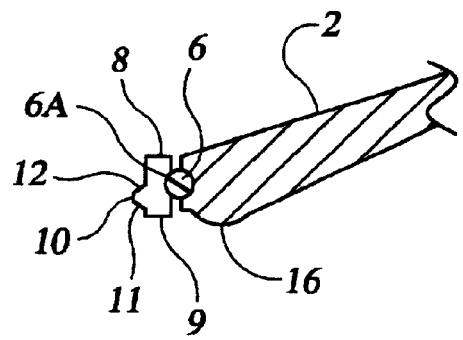
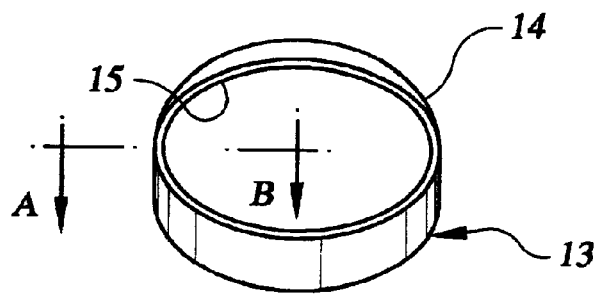
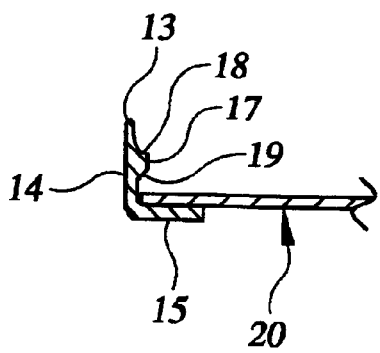
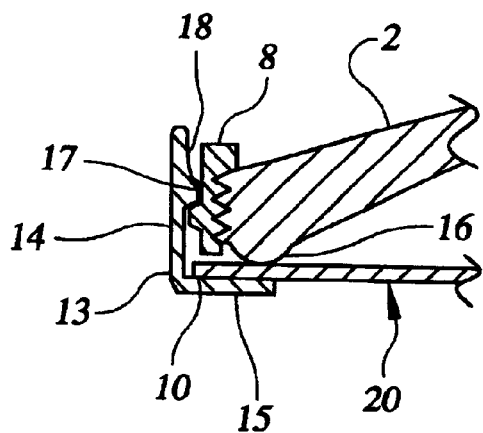

DIRECTION OF ROTATION OF PLATFORM 41

DISPOSABLE STETHOSCOPE DIAPHRAGM AND DISPENSER

This application is claiming the benefit of provisional application No. 60/138,765 filed on Jun. 11, 1999.

FIELD OF INVENTION

This invention relates to disposable diaphragm assemblies for stethoscopes used in the prevention of the spread of infectious diseases through the use of stethoscopes. More particularly, the present invention relates to both existing stethoscopes which may be retrofitted for the use of disposable diaphragm assemblies and to novel stethoscopes which have a main housing or body prepared for the use of the disposable diaphragm assemblies. The present invention also relates to dispensers, both stationary and portable, for the disposable diaphragm assemblies.

BACKGROUND OF THE INVENTION

Most common stethoscopes are designed with a retainer ring to hold a diaphragm in place. One such prior art stethoscope design is shown in FIGS. 1 and 2. The retainer ring 1 is attached to the stethoscope head 2 by means of threads 5. The retainer ring 1 is circular in shape having a vertically oriented side portion 4, the inside surface of which is threaded. Molded onto or attached onto the bottom face of such side portion 4 is a horizontally oriented lip portion 3 which extends toward the center of the circular retainer ring 1. A diaphragm 7 is held in place between lip portion 3 and the stethoscope head 2 upon threading or clipping the retainer ring 1 onto the stethoscope head 2. FIG. 3 shows an alternative prior art stethoscope design in which an O-ring 6 is used to hold the retainer ring 1 onto the stethoscope head. In each of these prior art devices, the diaphragm is changed by removing the retainer ring, removing the old diaphragm placing a new diaphragm in the retainer ring and re-attaching the retainer ring, Standard non-disposable diaphragms are generally not replaced between use on patients due to the time required to undertake such a change. As an alternative, the stethoscope head and diaphragm may be cleaned between uses. Such cleaning, however, may be detrimental to both the structural integrity and acoustical accuracy of the diaphragm, as such cleaning is often done with alcohol swabs. That is, both the difficulty in changing out diaphragms and the potential harm inflicted on diaphragms by cleaning act as barriers to the use of clean, uninfected stethoscope diaphragms.

The possibility of the transmission of infection between patients, where the stethoscope acts as the source of infection, is recognized in the medical community and is the subject of articles such as "Contaminated Stethoscopes: A Potential Source of Nosocomial Infections" by Mangi et al, Yale Journal of Biology and Medicine, 45,600–45,604 (1972) and "Contaminated Stethoscopes Revisited" by Melinda A. Smith, MPH, et al, Archives of Internal Medicine, Vol. 156 (1996).

A removable stethoscope diaphragm is the subject of U.S. Pat. No. 4,867,268 to Izaak Alan Ulert. It comprises a disposable diaphragm which replaces the diaphragm already in place on conventional stethoscopes. U.S. Pat. No. 4,461,368 to Plourde describes a diaphragm cover which is used for the prevention of the spread of infection from contaminated stethoscopes. The disposable diaphragm of the '368 patent interposes a second layer of material between the source of sound and the ear, which has the potential of diminishing or distorting the sound. Furthermore, the disposable diaphragm of the '368 patent is not easily or quickly interchanged. The lack of ease of use acts as a disincentive to use.

Completely disposable stethoscopes are also currently available. Such stethoscopes, however, do not offer the acoustic quality obtainable with standard stethoscopes. Dedicated stethoscopes are fairly expensive, thereby motivating repeated use which defeats the intended safety features.

There is a need, therefore, for a stethoscope device which provides high-quality acoustic performance in conjunction with an economical means of providing uninfected contact with each patient. Furthermore, there is a need that such device offer medical personnel ease of use with little or no preparation time.

SUMMARY OF THE INVENTION

The present invention addresses the shortcomings of the prior art devices by providing disposable diaphragm assemblies with acoustic performance which is equal to or greater than that of conventional stethoscopes. The present invention does not use a cover over the existing diaphragm of a conventional stethoscope as in the '368 patent. Therefore, the acoustic quality remains high and there is no additional sound attenuation which is present when multiple layers are placed between the source of the sound and the ear.

The disposable diaphragm assemblies of the present invention are inexpensive and therefore, may be changed out between uses so that only clean and uninfected portions of the stethoscope come into contact with a patient. The present invention also addresses the cleanliness and infection issue by providing dispensers for the disposable diaphragm assemblies which permit the disposable diaphragm assemblies to be attached to a stethoscope without contacting the diaphragm assemblies. Therefore, germs and contaminants are not transferred from the hands of medical personnel to patients.

The present invention provides means for retrofitting existing stethoscopes, including standard and open bell or pediatric stethoscopes. In addition, the present invention provides a novel stethoscope which may also be used with the disposable diaphragm assemblies of the present invention.

The present invention includes disposable diaphragm assemblies made of any suitable material, such as but not limited to plastic, rubber or other materials and dispensers stationary or portable, for such disposable stethoscope diaphragms.

BRIEF DESCRIPTION OF THE FIGURES

FIG. 4 is a partial cross-sectional view of the preferred embodiment of the universal retainer ring of the present invention.

FIG. 5 is a partial cross-sectional view of an alternative embodiment of the universal retainer ring of the present invention.

FIG. 6 is a top perspective view of the preferred embodiment of the holding ring of the disposable diaphragm assembly of the present invention.

FIG. 7 is a partial cross-sectional view of the preferred embodiment of the disposable diaphragm assembly of the present invention.

FIG. 8 is a partial cross-sectional view of the disposable diaphragm assembly of the present invention attached to a stethoscope head having a universal retainer ring of the present invention.

DETAILED DESCRIPTION OF THE INVENTION

Figure 1:
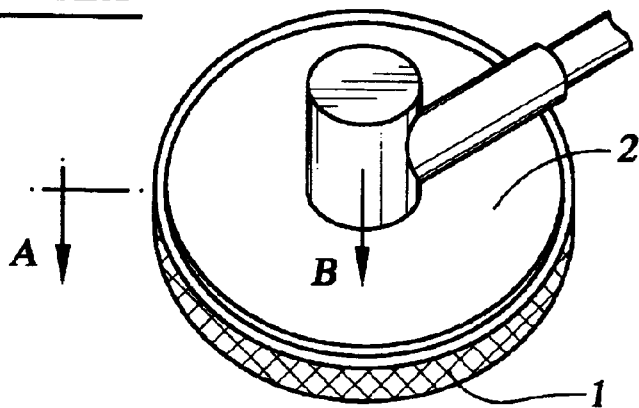
FIG. 1 is a perspective top view of a prior art stethoscope head and retainer ring design.
Figure 2:
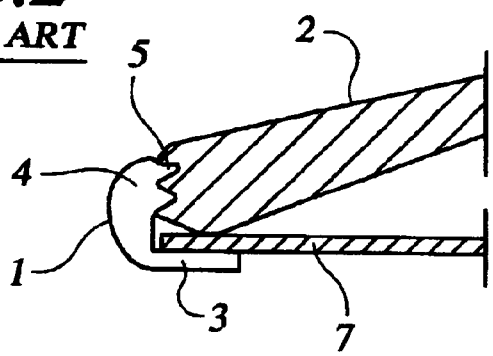
FIG. 2 is a partial cross-sectional view along the axis A–B of FIG. 1 of a prior art stethoscope head and retainer ring design.

Referring first to FIG. 4, the present invention utilizes a universal retainer ring 8 which is attached to a stethoscope head 2 from which its original retainer ring has been removed. The universal retainer ring 8 is circular in shape. Universal retainer ring 8 does not have the horizontally oriented lip portion present in retainer ring 1 described in connection with FIGS. 2 and 3. Where the original retainer ring was of the type shown in FIG. 2 which was attached to the stethoscope head by means of threads, the inside surface of the universal retainer ring 8 is threaded so as to attach onto the corresponding stethoscope head 2. Universal retainer ring 8 is sized such that the protrusion 16 on the stethoscope head 2 lies slightly below the bottom edge 9 of the universal retainer ring 8 when placed into position on stethoscope head 2.

Figure 3:
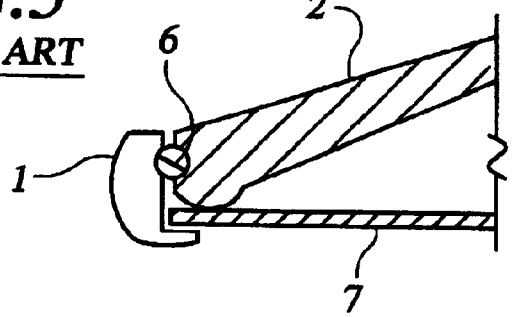
FIG. 3 is a partial cross-sectional view along the axis A–B of FIG. 1 showing an alternative prior art stethoscope and retainer ring design.

FIG. 5 shows an alternative embodiment of the universal retainer ring 8 which may be used for stethoscopes originally fitted with retainer rings of the type shown in FIG. 3 in which an O-ring is used to attach the retainer ring 1 onto the stethoscope head 2. As seen in FIG. 3, the inside surface of the illustrated universal retainer ring contains a semi-circular indentation 6A into which the O-ring 6 fits. It will be understood that the inside portion of the universal retainer ring 8 may be of any shape or configuration necessary to allow the universal retainer ring 8 to be fitted onto any existing stethoscope head 2. The embodiments shown in FIGS. 4 and 5 correspond to the most common currently available stethoscope designs.

Each embodiment of the universal retainer ring is equipped with a radial outwardly protruding tab 10 which is formed by outwardly and upwardly tapered portion 11 and outwardly and downwardly tapered portion 12. Tab 10 is used to hold the disposable diaphragm assembly of the present invention on the stethoscope head as is discussed in more detail in connection with FIG. 8. It will be understood that tab 10 may have other shapes or configurations, such as rounded, so long as such shape or configuration provides sufficient ease of removal and installation while yet providing sufficient hold so that the disposable diaphragm assembly stays in position during use. The configuration shown in FIGS. 4 and 5 is the preferred embodiment of the universal retainer ring of the present invention. Use of the universal retainer ring 8 permits the disposable diaphragm assembly of the present invention to be used with any common or specially designed stethoscopes.

The disposable diaphragm assembly of the present invention is comprised of two components, a holding ring and a disposable diaphragm. Both the holding ring and disposable diaphragm are intended to be disposed of and replaced after a single patient use. Referring now to FIGS. 6 and 7, the holding ring 13 is circular in shape having a vertically oriented side portion 14, the bottom edge of which is molded or attached onto a horizontally oriented lip portion 15. A disposable diaphragm 20 rests on horizontally oriented lip portion 15. The interior surface of side portion 14 of holding ring 13 has a radial inwardly protruding tab 17 which is formed by inwardly and downwardly tapered portion 18 and inwardly and upwardly tapered portion 19.

Referring now to FIG. 8, it can be seen that radial inwardly protruding tab 17 interconnects with radial outwardly protruding tab 10 of the universal retainer ring 8 so at hold the disposable diaphragm assembly in place. Referring still to FIG. 8, the disposable diaphragm assembly is shown attached to a stethoscope head 2 having a universal retainer ring 8. The diameter of outwardly protruding tab 10 of universal retainer ring 8 is slightly larger than the inside diameter formed by side portion 14 of holding ring 13. Consequently, when the disposable diaphragm assembly is attached to the stethoscope head/universal retainer ring combination, the two tabs 10 and 17 create a snapping type action and connection is made by pushing the stethoscope head 2 and universal retainer ring 8 combination into the holding ring 13. This also locks and retains the disposable diaphragm 20 in place. By snapping the universal retainer ring 8 and stethoscope head 2 into the holding ring 13, the disposable diaphragm 20 makes tight contact with the rounded extension 16 on the stethoscope head 2. This is important for proper sound transmittal.

The universal retainer ring 8 may be made from materials such as metal, plastic, or other suitable materials. The holding ring 13 is made from softer, flexible type materials such as, but not limited, to plastics. The difference of the materials and the associated flexible action of the holding ring 13 allows the snapping on and off of the holding ring 13 to the universal retainer ring 8.

The taper portions 11,12, 18 and 19 allow this on and off snapping action to be possible. The same tapers also assure proper retention of the disposable diaphragm assembly onto the stethoscope head 2. Furthermore, the taper portions 11, 12, 18, and 19 and protruding tabs 10 and 17 assure a tight fit connection of the disposable diaphragm 20 to the stethoscope head 2 and extension 16 which is very important for proper sound transmittal. Once a stethoscope is fitted with a universal retainer ring 8, disposable diaphragm assemblies may be simply snapped on or off.

Figure 9:
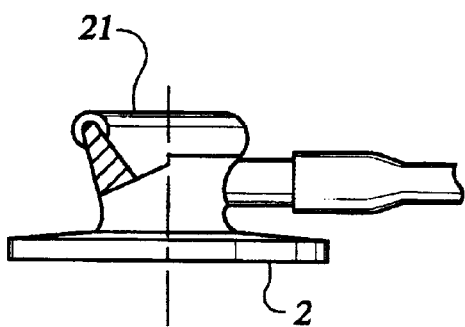
FIG. 9 is a side view, partially cross-sectioned, of a prior art combination standard and open bell stethoscope.
Figure 10:
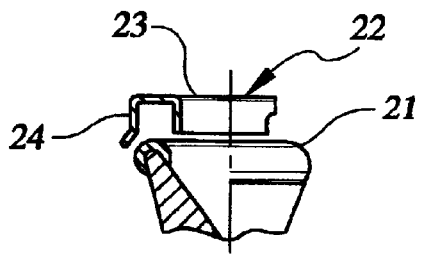
FIG. 10 is a partial side view, partially cross-sectioned, of a prior art open bell head and a ring type protective cover of the present invention.

Certain stethoscope heads, such as the open bell heads used in pediatric practice, as shown in FIG. 9, will not accommodate the universal retainer ring and disposable diaphragm assembly of the present invention. FIG. 9 shows a prior art stethoscope having both a typical stethoscope head 2 and an open bell head 21. FIG. 9 is partially cross-sectional to show the interior of the open bell head. An alternative disposable protective cover may be used with such open bell heads. Referring now to FIG. 10, a ring type protective cover 22 is shown. Protective cover 22 is in the general shape of a bottle cap, having a solid top surface 23 and a lower ring structure 24. FIG. 10 shows protective cover 22 in a partially cross sectional view to illustrate the ring structure 24. Such ring type protective cover 22 may utilize an adhesive means, such as a pressure sensitive adhesive, coated on the inside surface to assure retention of the protective cover 22 on the open bell head 21 during use. Alternatively, protective cover 22 may be made of some flexible material, such as a resilient plastic, and sized to fit snugly over the open bell head 21. Other suitable materials, include but are not limited to, rubber and paper. Protective cover 22 may be made in its entirety from the same material or in the alternative may be made from a plurality of materials. For example, the top surface could be made of paper attached to a ring structure composed of plastic.

Figure 11:
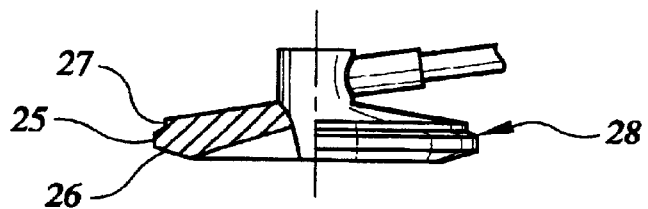
FIG. 11 is a side view, partially cross-sectioned, of a novel stethoscope head, constructed for use with the disposable diaphragm assembly of the present invention.

It will be understood that the disposable diaphragm assembly of the present invention could also be used with a stethoscope having a head designed in the shape of the universal retainer ring of the present invention. Such a stethoscope head 28 is shown in FIG. 11. The dimensions and shape of radial outwardly protruding tab 25 are identical to the dimensions and shape of the radial outwardly protruding tab 10 of the universal retainer ring 8. Similarly, tapered portions 26 and 27 are of the same size and shape as tapered portions 11 and 12, respectively, of universal retainer ring 8. Thus, the disposable diaphragm assembly of the present invention could be used with stethoscope head 28.

Figure 12:
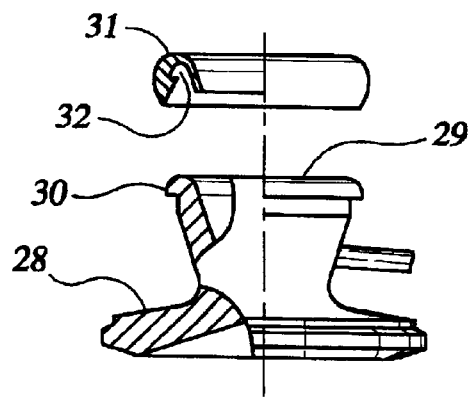
FIG. 12 is a side view, partially cross-sectioned, of a combination standard head and open bell head of the present invention and protective cover of the present invention.

In a similar manner, an open bell head could be specifically constructed to better hold a protective cover. Referring now to FIG. 12, a combination standard head and open bell head stethoscope is shown in which the standard head is shaped in the form of the universal retainer ring of the present invention, as discussed above in connection with FIG. 11. Open bell head 29 us formed with a outwardly protruding lip 30. A protective cover 31 attaches by means of snapping on to the open bell head 29 by interlocking an internal indentation 32 with lip 30. Protective cover 31 is made from a flexible material, such as plastic or rubber, allowing easy attachment and removal.

Figure 13:
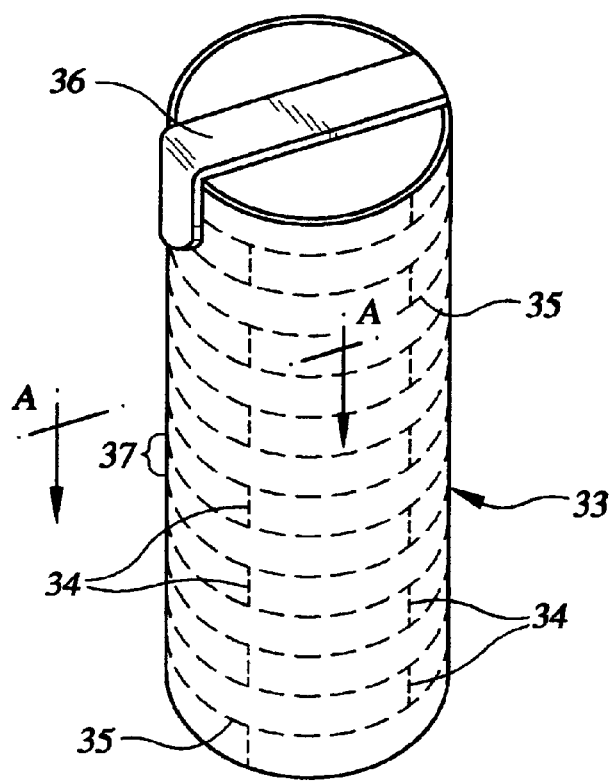
FIG. 13 is a perspective view of a preferred embodiment of the disposable, portable dispenser for the disposable diaphragm assembly of the present invention.

FIG. 13 shows a portable, disposable dispenser 33 for the disposable diaphragm assembly of the present invention. Dispenser 33 may be made from paper, card-board, plastic or other suitable materials and is designed to, hold a number of disposable diaphragm assemblies within its interior. The dispenser 33 is tubular in shape and sized to snugly hold the disposable diaphragm assembly of the present invention within the dispenser's interior diameter. Dispenser 33 is designed with perforations 34 and 35 and a removable, peel-off-type top 36. Dispenser 33 is further comprised of a bottom portion means for preventing the disposable diaphragm assemblies from falling out the bottom of the dispenser 33. Such means may include, without limitation, a cross-member extending across the bottom diameter or a flat integral bottom face. Perforations 35 run along the circumference of the dispenser 33 and are vertically spaced at intervals approximately equal to the height of a single disposable diaphragm assembly. Scored rings 37 are formed by perforations 35, the number of rings equaling the number of disposable diaphragm assemblies held within the dispenser 33. Perforations 34 run vertically across each scored ring 37 with the position of perforations 34 staggered in adjacent scored rings.

Figure 15:
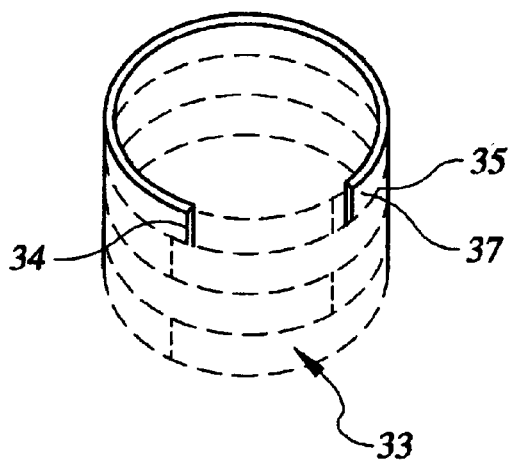
FIG. 15 is a perspective view of a preferred embodiment of the portable, disposable dispenser of the present invention illustrating a break in the topmost scored ring.
Figure 14:
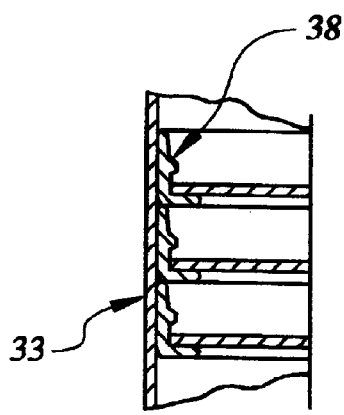
FIG. 14 is a side partial cross-sectional view, taken along the axis A—A of FIG. 13, of the portable, disposable dispenser of the present invention.

FIG. 14 is a partial cross-sectioned view of the dispenser 33 illustrating the stacking of disposable diaphragm assemblies 38 within the dispenser 33. Once the top 36 is removed, a stethoscope head 2 with the universal retainer ring 8 is inserted at an angle into the dispenser 33 to attach a disposable diaphragm assembly 38 to the retainer ring 8. As the stethoscope head/retainer ring is pressed down to snap into the disposable diaphragm assembly 38, holding ring 13 of the disposable diaphragm assembly 38 flexes outwardly causing scored ring 37 to fully or partially break open at its perforation 34, as shown in FIG. 15. After the disposable diaphragm assembly 38 is attached to the universal retainer ring 8, the broken scored ring 37 may be removed by peeling it off along the perforation 35.

Because the disposable stethoscope diaphragm assemblies 38 are stacked in the interior of the dispenser 33 with the interior, non-patient face of the disposable diaphragm 20 facing up, the patient side of the diaphragm 20 and the outer portion of lip portion 15 of holding ring 13, both of which come into contact with the patient are always clean prior to use.

Figure 16:
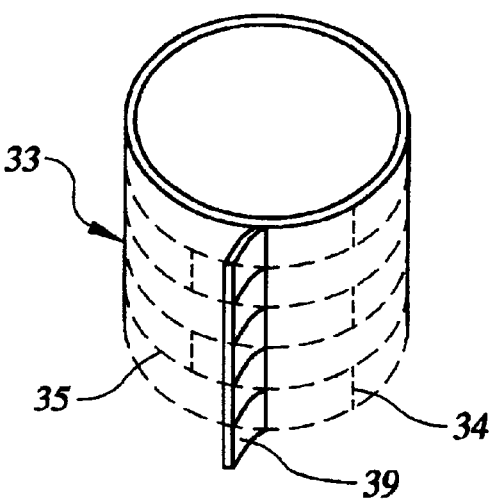
FIG. 16 is a perspective view of an alternative embodiment of the portable, disposable dispenser of the present invention.
Figure 17:
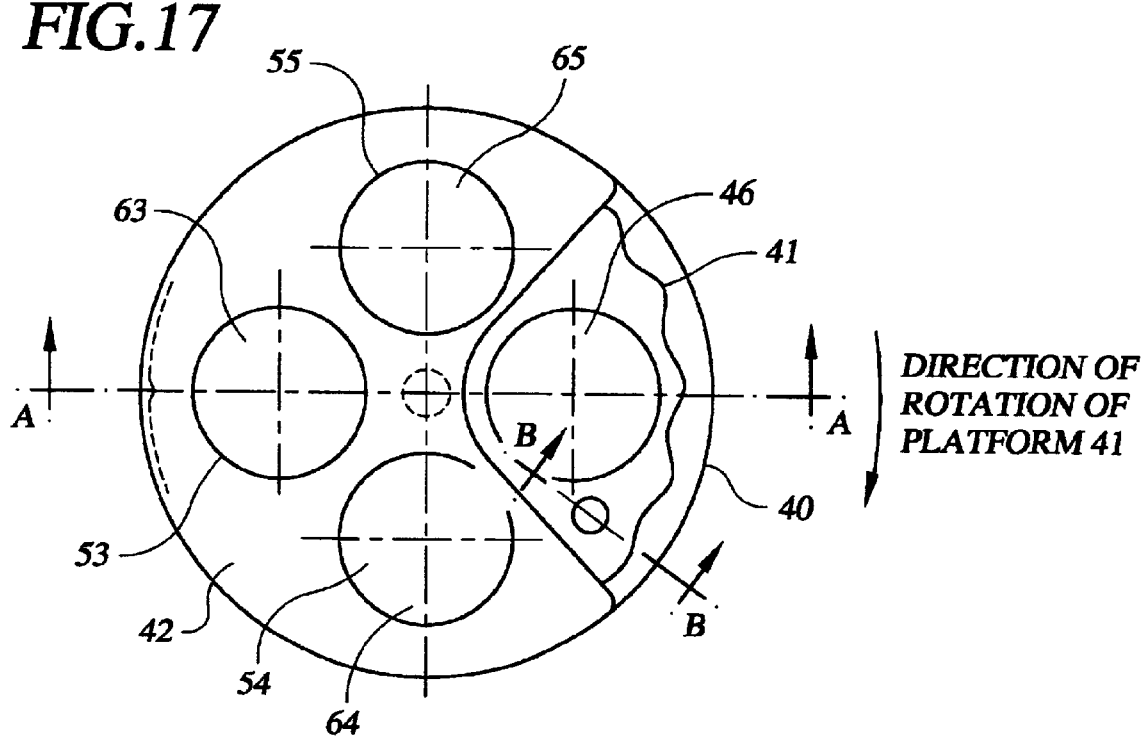
FIG. 17 is a top view of the preferred embodiment of the stationary dispenser of the present invention.
Figure 20:
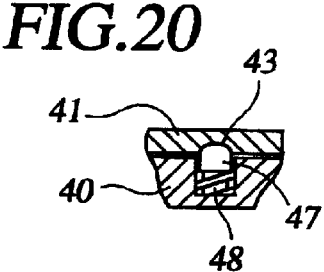
FIG. 20 is a cross-sectional view, taken along line B–B of FIG. 17 of the détente pin and recess of the stationary dispenser of the present invention.
Figure 19:
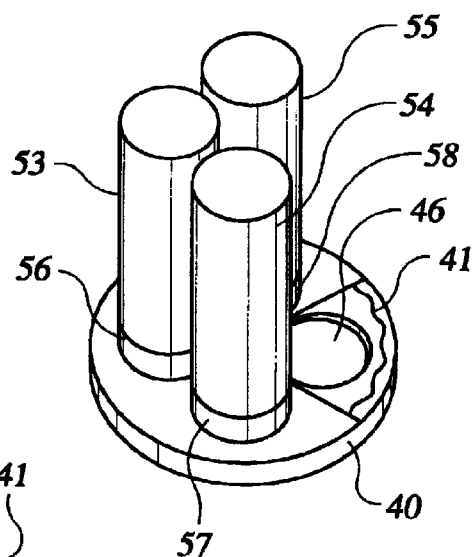
Figure 18:
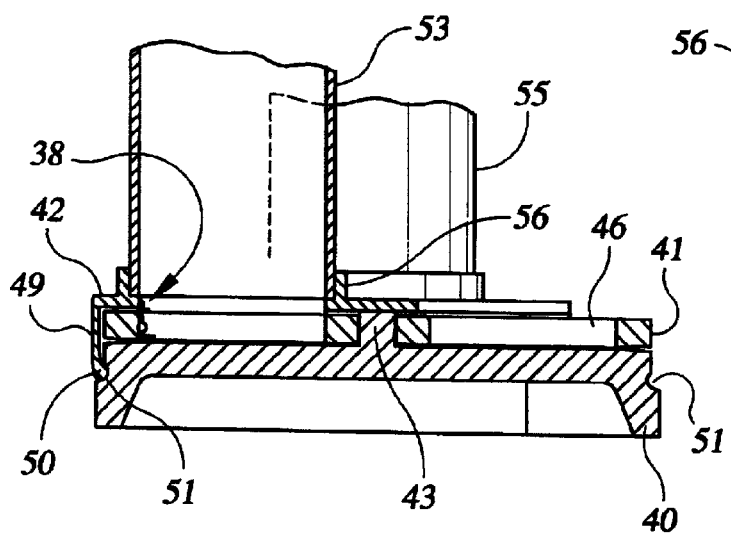
FIG. 18 is a cross-sectional view, taken along line A—A of FIG. 17, of the stationary dispenser of the FIG. 19 is a perspective view of the stationary dispenser of the present invention.

FIG. 16 displays an alternative embodiment of a dispenser 33 in which each scored ring 37 is further comprised of an outwardly projecting pull tab 39 used to remove a broken scored ring 37 from the dispenser 33.

A stationary dispenser 70 is illustrated in FIGS. 17–20. The stationary dispenser is comprised of three platforms, shown as 40, 41, and 42. Platform 40 is the base platform and has a raised projection at its center called the pivot point 43. Pivot pin 43 protrudes upward into a recess in the bottom surface of platform 41. This allows platform 41 to rotate on top of platform 40. The outside diameter of platform 41 has a wavy configuration. This wavy configuration allows easy rotation by hand of platform 41. It will be understood that motorized rotation may also be accomplished by actuating a motor and associated switches and timers. Such motorized methods and related devices are commercially available and may be incorporated into the present invention by one of skill in the art. Platform 41 has four circular recessed areas 46, 63, 64 and 65, the interior diameter and depth of which are slightly larger than the outside diameter of the disposable diaphragm assembly 38.

Platform 42 is three-quarters circular in shape and sits above platform 41 without interfering with the rotation of platform 41. Platform 42 is connected to platform 40 through a horizontal lip 49 which protrudes downward around platform 41. Lip 49 contains a projection 50 which snaps into an indentation 51 on platform 40. That is, platform 41 is rotatably sandwiched between platforms 40 and 42. Because platform 42 is not completely circular, a section of platform 41 and the recess 46 in platform 41 is exposed.

Stationary dispenser 70 is further comprised of three tubular containers, 53, 54, and 55, extending upward from platform 42. Platform 42 is further comprised of three tubular receptacles 56, 57 and 58, which extend upwardly from the top surface of platform 42 and which are equally spaced at 90 degrees from each other. Tubular receptacles 56, 57 and 58 are sized such that tubular containers 53, 54, and 55 can be inserted and contained securely within the receptacles.

Each of tubular container 53, 54 and 55 hold a number of disposable diaphragm assemblies. The number of disposable diaphragm assemblies which each tubular container can accommodate depends upon the length of the containers. A tubular container of eight inches in height will hold about thirty-two disposable diaphragm assemblies. It will be understood that in an alternative embodiment, tubular containers 53, 54 and 55 may be unitarily molded as a part of and extending upwardly from platform 42.

Platform 40 is further comprised of a detente pin 47 and a spring 48. The detente pin 47 mates one of four recesses 43 in platform 41. The four recesses 43 are placed 90 degrees apart on the bottom surface of platform 41 and are located to assure proper location of the containers 53, 54 and 55 over the recessed areas 63, 64 and 65. The three tubular containers 53, 54 and 55 are filled with disposable diaphragm assemblies and sit on top of platform 42 over the recessed areas 63, 64 and 65. Thus the recesses 63, 64 and 65 accept the lowermost disposable diaphragm assemblies in each of containers 53, 54 and 55, respectively. As the platform 41 is rotated from détente recess to the next detente recess 43, a disposable diaphragm assembly is exposed. In this position of platform 41 with a disposable diaphragm assembly inside the recess 46, a stethoscope prepared with the universal retainer ring 8 or configured as described in connection with FIG. 11 or 12 may be inserted in recess 46 and the disposable diaphragm assembly 38 may be attached to the stethoscope.

Disposable diaphragm assemblies are stacked within containers 53, 54 and 55 such that the interior portions of the disposable diaphragm assemblies are facing up. Thus, those surfaces which come into contact with a patient are kept clean until used.

The rotational process of platform 41 is repeated to locate the next disposable diaphragm assembly in recess 46 of the platform 41. The rotation of platform 41 may be repeated until all containers 53, 54 and 55 are empty.

In an alternative embodiment of the stationary dispenser of the present invention, an openable cover 61 (not shown) in the size and shape to cover the exposed recess 46 may be added to platform 42. Cover 61 would protect any unused disposable diaphragm assembly within recess 46 until needed. When in use, cover 61 would be opened to expose recess 46 and a new disposable diaphragm assembly so that the assembly could be attached to a stethoscope.

It will be understood that a number of configurations for dispensers, both stationary and portable/disposable, are possible. In the present invention, the critical element for such dispensers is the ability to load a disposable diaphragm assembly without contaminating the assembly with the hands of medical personal. The dispensers of the present invention accomplish this goal by maintaining the cleanliness of the assemblies while the assemblies are stored in the dispenser and while the assemblies are loaded onto stethoscopes.

While a limited number of the embodiments of the present invention have been discussed herein, it will be understood that the invention is-not limited but rather that various alterations could be made on the present invention without departing from the scope of the invention.

We claim:

1. A diaphragm assembly for use with a modified standard stethoscope having an outer rim from which a standard retaining ring has been removed, further having a stethoscope head extension and further from which a standard diaphragm has been removed, comprising:
    a universal retaining ring comprising
        an interior face having means for connecting to said outer rim of said modified standard stethoscope; and
        an exterior face having a circumferentially outwardly protruding ridge;
    a holding ring having a horizontally oriented lip portion, said lip portion having an outward face and an inward face and a vertically oriented side portion wherein said side portion extends upward from said lip portion to a distance greater than the size of the head of said modified standard stethoscope;
        said side portion having an interior face, said interior face having a circumferentially inwardly protruding ridge, said ridge flanked by first and second tapered portions; and
    a replacement diaphragm positioned upon said inward face of said lip portion, such that when said diaphragm assembly is attached to said modified standard stethoscope said replacement diaphragm is in contact with said stethoscope head extension.

2. The diaphragm assembly of claim 1 wherein said replacement diaphragm is unitarily molded onto said lip portion of said holding ring.

3. The diaphragm assembly of claim 1 wherein said means for connecting to said outer rim of said modified standard stethoscope comprises threads.

4. The diaphragm assembly of claim 1 wherein said means for connecting to said outer rim of said modified standard stethoscope comprises a semi-circular indentation.

5. A portable and disposable dispenser comprising:
    a tubular body having a plurality of circumferential perforations, said circumferential perforations forming a plurality of scored rings;
        said tubular body having top and bottom ends;
    each of said scored rings having a horizontal perforation across the height of said scored rings;
    a removable top closure means located at said top end of said tubular body; and
    means for closing said bottom end of said tubular body.

6. The portable and disposable dispenser of claim 5 wherein said tubular body is made of plastic.

7. The portable and disposable dispenser of claim 5 wherein said tubular body is made of cardboard.

8. The portable and disposable dispenser of claim 5 further comprising:
    a plurality of radial outwardly projecting tabs, each of said scored rings having one said tab.

9. A stationary dispenser comprising:
    a base platform having a central pivot pin;
    a rotating platform having a plurality of recessed areas, said recessed areas sized slightly larger than said disposable diaphragm assembly of claim 1 and having a plurality of détente recesses;
        said rotating platform having a central opening or cavity, said opening or cavity resting upon said pivot pin of said base platform;
    a top platform placed above said rotating platform, said top platform having means to connect to said base platform such that said rotating platform may freely rotate;
        said top platform having a cut-out area such a portion of said rotating platform is exposed;
        said top platform having a plurality of tubular receptacles extending upward from said top platform;
    a plurality of tubular containers, said tubular containers of a size and shape to enclose said disposable diaphragm assemblies of claim 1; and
    said tubular containers sized to fit within said tubular receptacles.

* * * * *